(12) United States Patent
Yang (10) Patent No.: US 11,246,976 B2
(45) Date of Patent: Feb. 15, 2022

(54) DELIVERY SYSTEM OF PORTABLE DELIVERY DEVICE

(71) Applicant: MEDTRUM TECHNOLOGIES, INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 382 days.

(21) Appl. No.: 16/321,940

(22) PCT Filed: Aug. 12, 2016

(86) PCT No.: PCT/CN2016/094979
§ 371 (c)(1),
(2) Date: Jan. 30, 2019

(87) PCT Pub. No.: WO2018/027944
PCT Pub. Date: Feb. 15, 2018

(65) Prior Publication Data
US 2019/0175819 A1 Jun. 13, 2019

(51) Int. Cl.
*A61M 5/14* (2006.01)
*A61M 5/142* (2006.01)
(Continued)

(52) U.S. Cl.
CPC ........ *A61M 5/1413* (2013.01); *A61M 5/1452* (2013.01); *A61M 5/14248* (2013.01);
(Continued)

(58) Field of Classification Search
CPC ............ A61M 5/1413; A61M 5/14248; A61M 5/1452; A61M 5/162
See application file for complete search history.

(56) References Cited

U.S. PATENT DOCUMENTS 5,176,662 A * 1/1993 Bartholomew ... A61M 25/0606
128/DIG. 26
6,939,324 B2 * 9/2005 Gonnelli ........... A61M 5/14593
604/142
(Continued)

FOREIGN PATENT DOCUMENTS

CN 203647799 U 6/2014
CN 106110445 A 11/2016
(Continued)

OTHER PUBLICATIONS

European Patent Application No. 16912399.9: Extended European Search Report dated Dec. 5, 2019, 7 pages.

*Primary Examiner* — Manuel A Mendez
(74) *Attorney, Agent, or Firm* — JCIP Global Inc.

(57) ABSTRACT

A delivery system of a portable delivery device, using a chamber with three connections structure (10) arranged on the upper housing (1) as a buffer channel for the flow passage of the drug fluid from the external syringe into the reservoir (6) and from the reservoir (6) into the infusion needle; and the structures on the upper, the lower housings (1), (4) and the needle seat (2) accommodating the infusion needle mate with each other sophisticatedly ensuring the compactness of the delivery device and enabling the patient to control the position of the infusion needle safely and conveniently at the same time; in additional, the needle seat cover (7, 8) which covers the needle seat (2) enhances the safety of using the infusion needle. The delivery system of a portable delivery device has advantages of small size, sophisticated structure, simple operation, safety guarantee.

15 Claims, 7 Drawing Sheets

(51) Int. Cl.
  *A61M 5/145* (2006.01)
  *A61M 5/162* (2006.01)
  *A61M 5/158* (2006.01)

(52) U.S. Cl.
  CPC ... *A61M 5/162* (2013.01); *A61M 2005/14252* (2013.01); *A61M 2005/1583* (2013.01); *A61M 2005/1585* (2013.01)

(56) References Cited

U.S. PATENT DOCUMENTS

| | | |
|---|---|---|
| 9,265,881 B2 * | 2/2016 | Montalvo ......... A61M 5/16831 |
| 2007/0066955 A1 | 3/2007 | Sparholt et al. |
| 2008/0269687 A1 | 10/2008 | Chong et al. |
| 2013/0066281 A1 | 3/2013 | Yavorsky et al. |
| 2014/0052096 A1 | 2/2014 | Searle et al. |
| 2016/0082182 A1 | 3/2016 | Gregory et al. |

FOREIGN PATENT DOCUMENTS

| | | |
|---|---|---|
| EP | 2420276 A2 | 2/2012 |
| WO | WO 2014/194183 A2 | 12/2014 |

* cited by examiner

DELIVERY SYSTEM OF PORTABLE
DELIVERY DEVICE

CROSS-REFERENCE TO RELATED
APPLICATIONS

This application is the National Stage of International Patent Application No. PCT/CN2016/094979, filed Aug. 12, 2016, the disclosure of which is incorporated herein by reference in its entirety.

TECHNICAL FIELD

The present invention generally relates to the field of medical appliance, specifically to a delivery system of a portable delivery device.

BACKGROUND OF THE INVENTION

A fluid delivery device is a medical device which can treat disease by continuously delivering a fluid into a patient. The fluid delivery device is widely used in the treatment of diabetes by continuously delivering insulin to a subcutaneous tissue of a patient based on a dosage required, so as to simulate the secretion function of the pancreas and stabilize glucose of the patient. The fluid is usually stored in a reservoir, and a conventional fluid delivery device usually delivers the fluid into a patient via a tubing connected to the reservoir. The tubing, when it is used, is not only an obstruction for the patient's activities, but also not pleasant to the eye.

In order to overcome the above-mentioned shortcomings of the conventional fluid delivery device, a tubing-free fluid delivery device has been developed, comprising a pump device which can be stuck to a human body using a medical tape with an indwelling cannula implanted in a subcutaneous tissue in order to deliver a fluid. Referring to the aspect of the passage of the fluid, firstly fill the cartridge with a syringe or use a prefilled cartridge, then the fluid is delivered to the patient by an infusion needle or a cannula implanted subcutaneously. For delivery device with a prefilled cartridge, a prefilled cartridge arranged in the delivery device is required, and the cartridge or the whole delivery device has to be replaced after the fluid prefilled in the cartridges has been delivered, causing waste of other members whose uses are sustainable. Additionally, the way of replacing the whole delivery device by a new one every time using up the fluid stored in a prefilled cartridge only suits the low-cost mechanical pump device without sophisticated and expensive electronic components. For another kind of delivery device, the fluid is filled into a cartridge directly then delivered to a human body by an infusion needle coupled with the cartridge. However, a special supporting injection device is required meaning the universal syringe cannot be used, causing more disposables and higher cost, which is also not conducive to the wide application of the delivery device. How to design the passage of the drug fluid from filling the pump to delivering to a patient with the simplest structure based on the requirement of compactness which cannot be compromised, is indispensable to an advanced portable delivery device.

SUMMARY OF THE INVENTION

To overcome shortcomings in the prior art mentioned above, a purpose of the present invention is to provide a delivery system of a portable delivery device, comprising:

an upper housing, wherein the upper housing comprises a chamber with triple connections to a syringe, a reservoir and an infusion needle;

a lower housing mating the upper housing;

a reservoir arranged inside the upper housing with a hole on it;

an infusion needle.

Alternatively, the chamber with triple connections is connected with the syringe, the reservoir and the infusion needle by three elastic material components.

Alternatively, a hole is set on the elastic material element connecting the chamber with triple connections and the reservoir, mating the hole on the reservoir.

Alternatively, the infusion needle is a U-shape hollow needle.

Alternatively, the U-shape hollow needle is arranged on a needle seat which is installed on a needle seat container on the upper housing movably.

Alternatively, the U-shape hollow needle has two ends of different lengths;

the short end is connected with the chamber with triple connections by penetrating the elastic material element, configured to allow the drug fluid to enter the lumen of the U-shape hollow needle from the chamber with triple connections;

the long end of the U-shape hollow needle is able to penetrate a human skin through the upper housing and the lower housing, configured to deliver the drug fluid to human body from the lumen of the U-shape hollow needle.

Alternatively, the needle seat comprises a needle fixing column, configured to fix the long end of the U-shape hollow needle on the needle seat; further comprises a multi-cavity column with an outer rim;

the needle seat container on the upper housing comprises two receiving cavities, one cylindrical cavity is configured to receive the needle fixing column; the other cavity is configured to receive the multi-cavity column and mate with the outer rim of the multi-cavity column, preventing the needle seat from being separated completely from the upper housing.

Alternatively, a slidable button with a tiny hook which releasably mate the multi-cavity column is further set on the upper housing, configured to control the position of the needle seat.

Alternatively, the lower housing comprises a column and a receiver with an exit hole which allows the infusion needle to go through.

Alternatively, a spring is set around the column on the lower housing, cooperating with the slidable button, configured to retract the needle seat after the needle seat being pressed in order to withdraw the infusion needle into the lower housing.

Alternatively, the multi-cavity column has an irregular shape and comprises two cavities I and II;

cavity I is configured to receive the column with the spring on the lower housing, and the multi-cavity column has an outer rim near cavity I configured to get the multi-cavity column stuck on the upper housing, preventing the needle seat from being separated completely from the upper housing;

cavity II is configured to mate the tiny hook on the slidable button, and a slot is further arranged on the multi-cavity column from which the tiny hook can be released from cavity II.

Alternatively, a needle seat cover with a latch is releasably installed on the needle seat;

a hole is set on the upper housing and a hole is set on the multi-cavity column of the needle seat;

the two holes initially overlap each other and the latch is inserted in the two holes, configured to prevent the needle seat from being pressed improperly making the infusion needle protruding from the lower housing.

Alternatively, a needle seat cover is releasably half-covered the combined upper and lower housings;

the top part of the needle seat cover covers the upper surface of needle seat, and the bottom part of the needle seat cover covers the exit hole of the infusion needle on the lower housing, preventing the infusion needle protruding from the lower housing.

Alternatively, the elastic material components are silicone keys.

Alternatively, the lower housing further comprises several tiny holes for air permeation.

Compared to prior arts, the present invention has advantages in the following ways: firstly, a buffer channel is created for the flow passage of the drug fluid from the external syringe into the reservoir and from the reservoir into the infusion needle using a chamber with three connections structure arranged on the upper housing, a common syringe can be used to fill the reservoir, and the reservoir can be refilled for multiple times after using up the drug fluid stored in the reservoir; secondly, the structures on the upper, the lower housings and the needle seat accommodating the infusion needle mate with each other sophisticatedly ensuring the compactness of the delivery device and enabling the patient to control the position of the infusion needle safely and conveniently at the same time; Last but not least, the needle seat cover which covers the needle seat enhances the safety of using the infusion needle, one style of the needle seat covers also helps exhaust air from the needle. To sum up, the delivery system of a portable delivery device in the present invention has advantages of small size, sophisticated structure, simple operation, safety guarantee, meeting the patients' requirements for both compactness and excellent and reliable performance of a portable delivery device.

DETAILED DESCRIPTION

To make the above-mentioned objects, features and advantages of the present invention more obvious and understandable, the embodiments of the present invention are described in the following through specific embodiments.

Figure 1:
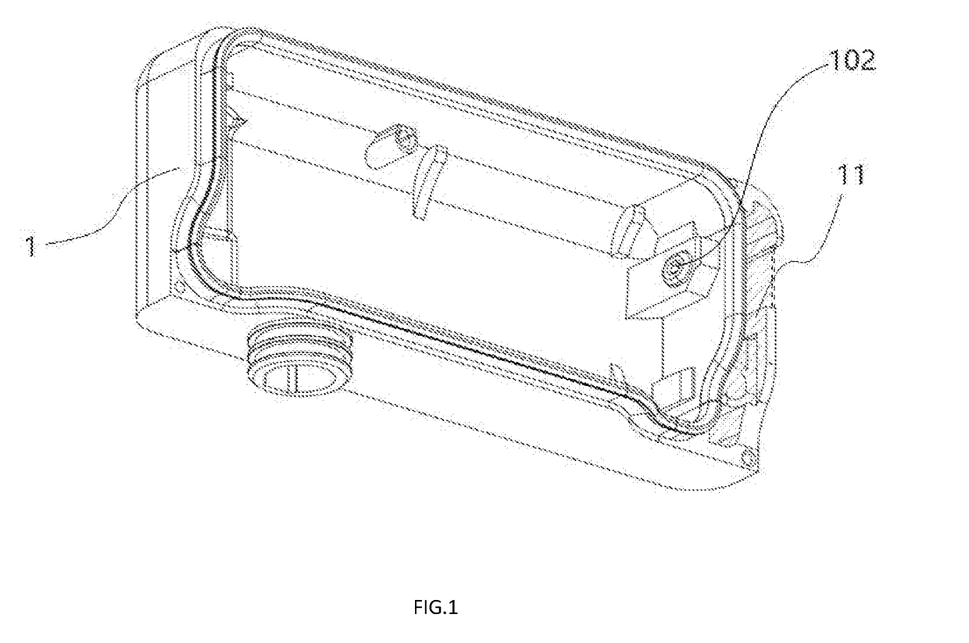
FIG. 1 is a perspective view of the upper housing of the delivery system of a portable delivery device in the present invention
Figure 2:
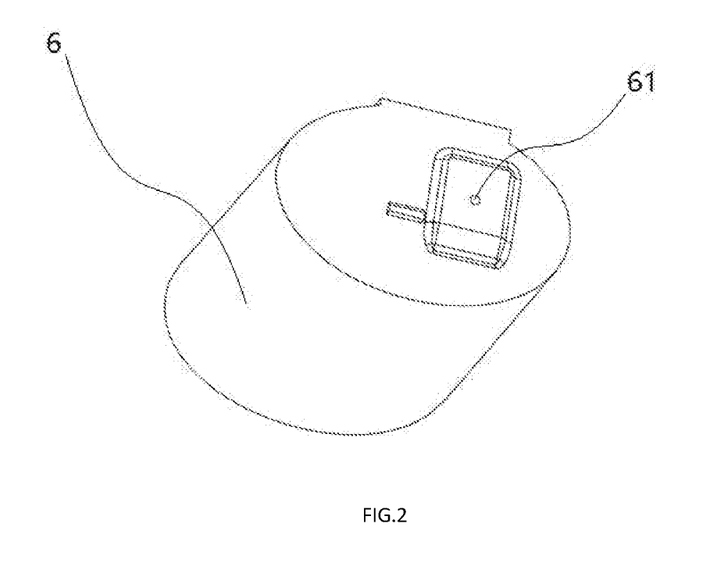
FIG. 2 is a perspective view of the reservoir of the delivery system of a portable delivery device in the present invention

Referring to FIG. 1 and FIG. 2, an embodiment of an upper housing and a reservoir of the delivery system of a portable delivery device in the present invention is provided. As shown in FIG. 1, the volume of an upper housing 1 generally comprises two parts, a needle seat container 11 configured to accommodate a needle seat and the rest part configured to accommodate a reservoir 6 as shown in FIG. 2 and other components. The two parts are structurally separated from each other, and a chamber with triple connections is arranged in the structure by which the upper housing 1 is separated into these two parts. The chamber with triple connections has a bump part facing the reservoir 6 with a silicone key 102 embedded in, and the silicone key 102 is one of the three components connecting the chamber with triple connections with other parts in the delivery system realizing the filling and delivery of the drug fluid. A hole is set on the silicone key 102 which can be connected with a hole 61 set on the reservoir 6 as shown in FIG. 2, configured to connect the reservoir 6 and the chamber with triple connections.

Figure 3:
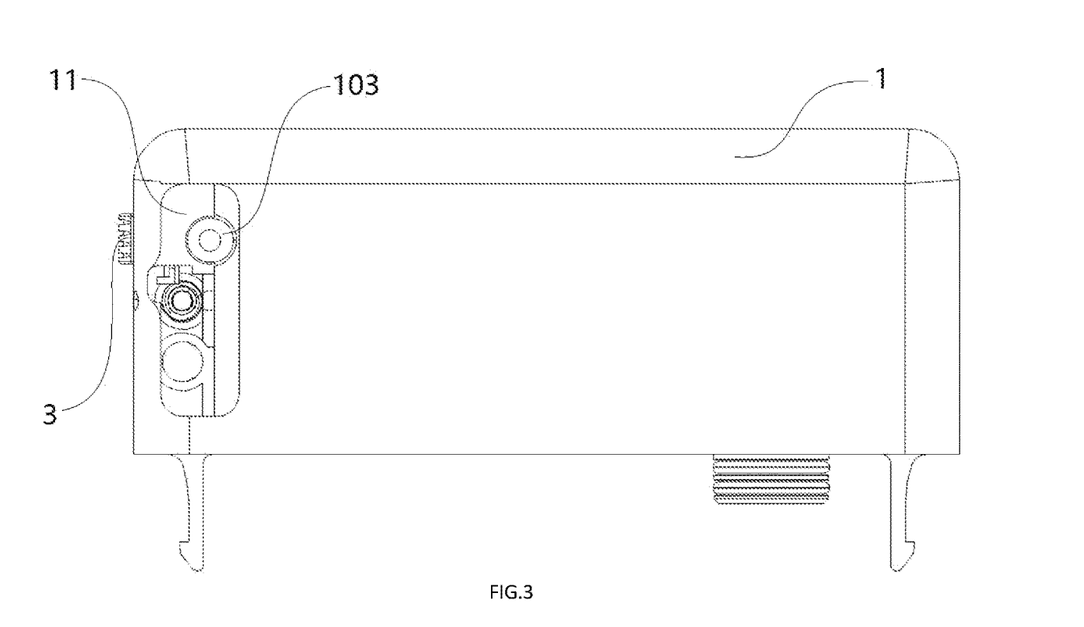
FIG. 3 is a plan view of the upper housing of the delivery system of a portable delivery device in the present invention
Figure 4:
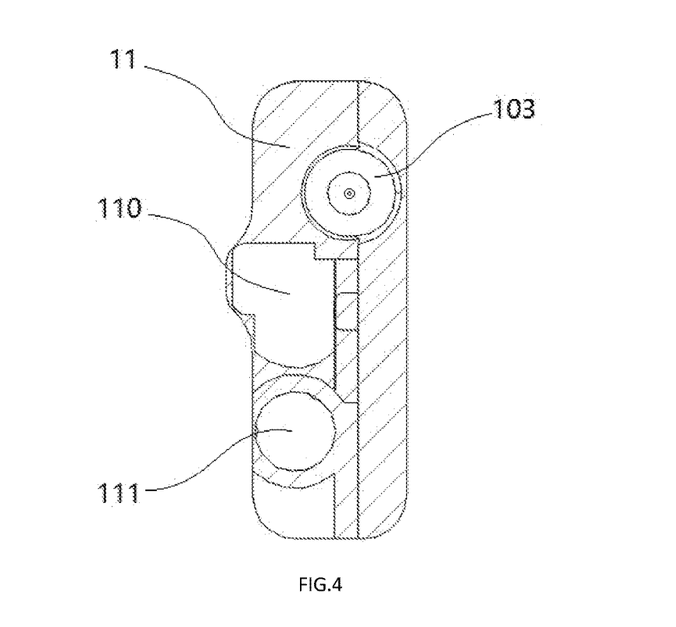
FIG. 4 is a partial enlarged plan view of the upper housing of the delivery system of a portable delivery device in the present invention
Figure 5:
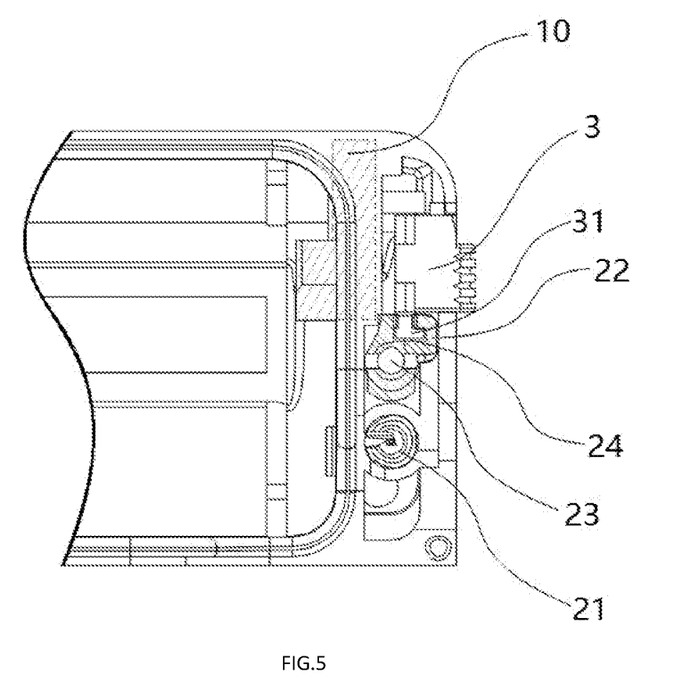
FIG. 5 is a bottom view of the upper housing with the needle seat of the delivery system of a portable delivery device in the present invention

Referring to FIG. 3 to FIG. 5, an embodiment of an upper housing with a needle seat container is provided. As shown in FIG. 3, a needle seat container 11 is set at one side of the upper housing 1, and a slidable button 3 is set near the needle seat container 11 on the outer side wall of the upper housing 1. As shown in FIG. 4, the needle seat container 11 comprises two receiving cavities, one cylindrical cavity 111 is configured to accommodate the needle fixing column 21 on the needle seat as shown in FIG. 5; the other cavity with an irregular shape 110 is configured to accommodate the multi-cavity column 22 on the needle seat as shown in FIG. 5. A silicone key 103 is further set on the upper housing 1 as shown in FIG. 4, configured to connect the lumen of a U-shape needle and the chamber with triple connections via being penetrated by a short end of the U-shape needle.

Figure 7:
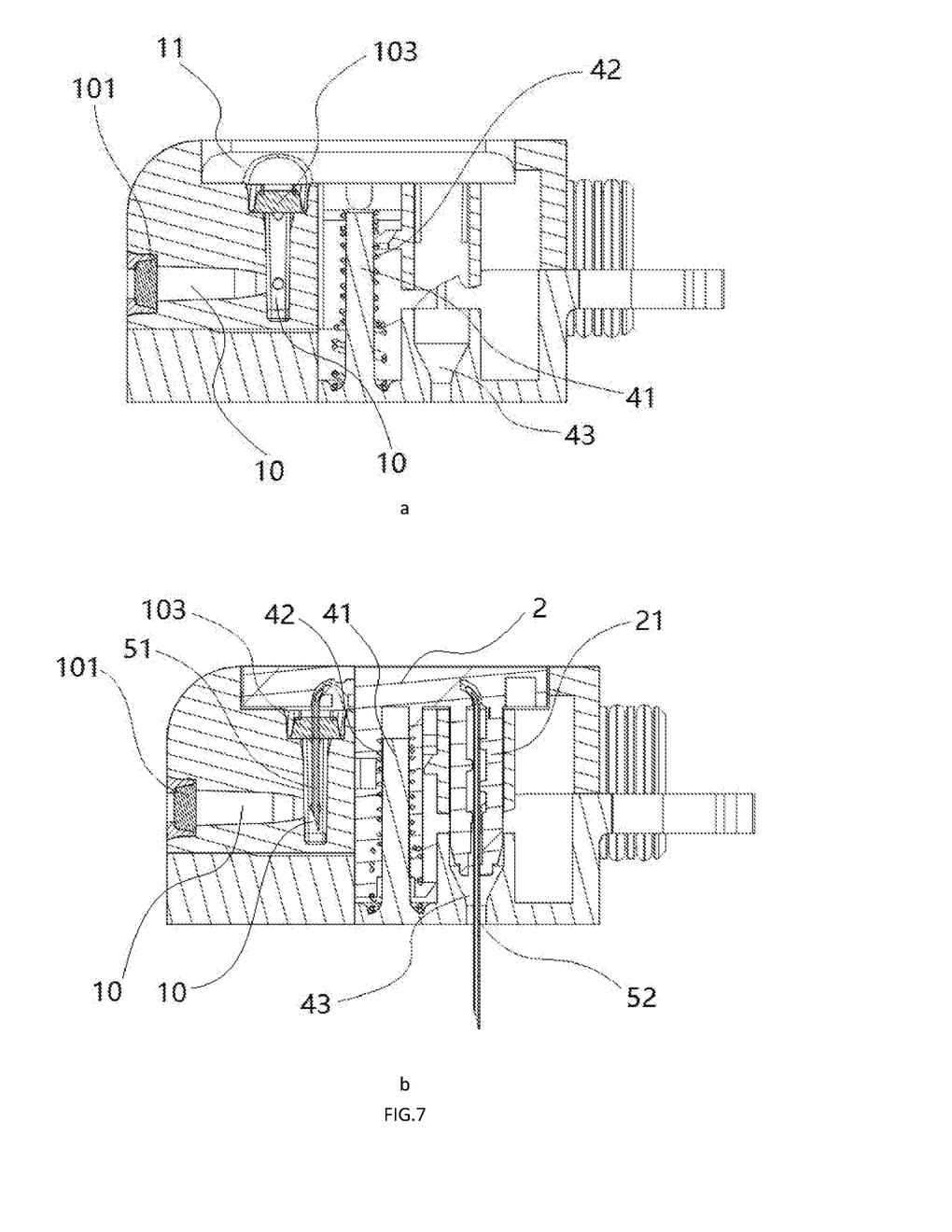
FIG. 7 is a partial cross-sectional view of the delivery system of a portable delivery device in the present invention

Referring to FIG. 5 to FIG. 9, an embodiment of how the structures on the needle seat, the upper housing, and a lower housing needle mate with each other is provided. As shown in FIG. 5, the chamber with triple connections 10 is a buffer channel of the drug fluid with an irregular shape arranged in the separating structure of the upper housing 1 separating the needle seat container 11 from the rest part in the upper housing 1. A slidable button 3 with a tiny hook 31 which releasably mates a multi-cavity column 22 of the needle seat is further set on the side wall of the upper housing 1, configured to switch the needle seat between an initial position and an engaged position. As shown in FIG. 5, the multi-cavity column 22 of the needle seat also has an irregular shape with two cavities; one cavity 23 is configured to accommodate the column 41 with a spring 42 on the lower housing as shown in FIG. 7, and the other cavity 24 is configured to mate the tiny hook 31 on the slidable button 3, and a slot 221 as shown in FIG. 7a is further arranged on the multi-cavity column 22 from which the tiny hook 31 can be released from the cavity 24.

Figure 6:
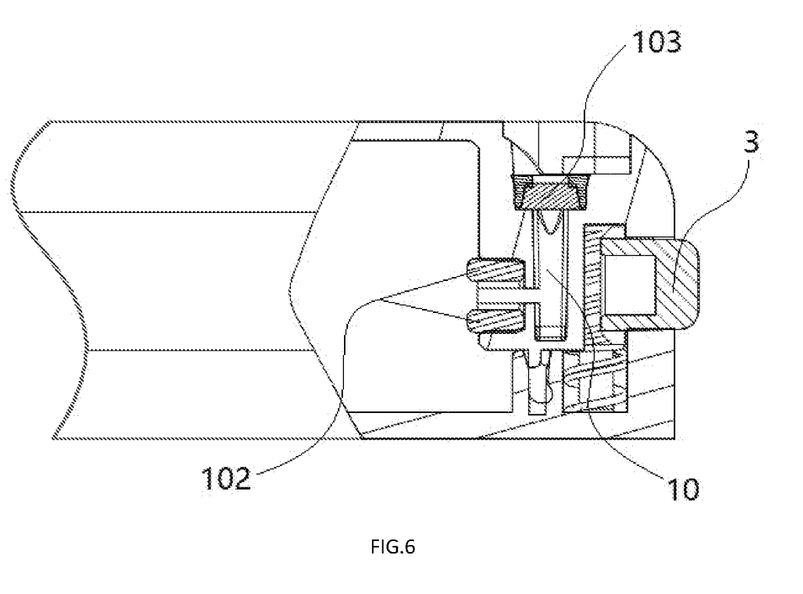
FIG. 6 is a partial cross-sectional side view of the upper housing of the delivery system of a portable delivery device in the present invention

FIG. 6 shows two silicone keys 102 and 103 connecting the chamber with triple connections 10 to the reservoir and the short end of the U-shape needle. When the reservoir is set ready in the upper housing, the silicone key 102 embedded in the bump part of the upper housing as shown in FIG. 1 is pressed against a slightly bulged part on the reservoir 6 as shown in FIG. 2 tightly to avoid leakage, and the hole set on the silicone key 102 is connected with the hole 61 on the reservoir 6 as shown in FIG. 2 to enable the flow passage of drug fluid from the chamber with triple connections 10 to the reservoir 6 or reversely.

Referring to FIG. 6 and FIG. 7, an embodiment of how the drug fluid goes from a syringe to a reservoir through the chamber with triple connections is provided. As shown in FIG. 7, another silicone key 101 connecting the chamber with triple connections 10 and a syringe which is not shown in the drawings is set on a side wall near the needle seat container 11 different than the side wall which comprises the slidable button 3 of the upper housing. When a reservoir needs to be filled, use a needle of a syringe containing the drug fluid needed to penetrate the silicone key 101, so the drug fluid goes into the chamber with triple connections 10 from the syringe through the silicone key 101 as shown in FIG. 7 and goes into the reservoir through the silicone key 102 as shown in FIG. 6.

Referring to FIG. 6 and FIG. 7, the silicone key 103 connects the chamber with triple connections 10 to the lumen of the U-shape needle. FIG. 7a illustrates a cross-sectional view of how the upper and lower housings are mated without the needle seat, and FIG. 7b illustrates a cross-sectional view of how the U-shape needle installed on the needle seat 2 is interacted with the structures on the upper and lower housings. As shown in FIG. 7b, when the needle seat 2 is pressed onto the needle seat container on the upper housing, the short end 51 of the U-shape needle penetrates the silicone key 103 connecting the lumen of the U-shape needle and the chamber with triple connections 10; while the long end 52 of the U-shape needle fixed on the needle fixing column 21 of the needle seat 2 goes through an exit hole of a receiver 43 on the lower housing and penetrates a human skin. When a delivery is needed, a piston in the reservoir which is not illustrated in the drawings is pushed by a drive unit of the portable delivery device, and the drug fluid which has been filled into the reservoir from a syringe goes back into the chamber with triple connections 10 from the reservoir via the hole on the silicone key 102 as shown in FIG. 6 and the hole 61 on the reservoir as shown in FIG. 2, and further goes into the lumen of the U-shape needle from the short end 51 penetrating the silicone key 103 and eventually goes into the human body from the long end 52 of the U-shape needle going through a receiver 43 with an exit hole on the lower housing as shown in FIG. 7b.

As shown in FIG. 7, a column 41 with a spring 42 around on the lower housing 4 is located between the short end 51 and the long end 52 of the U-shape needle from a side view when the upper housing is coupled with the lower housing, configured to pull the needle seat 2 out of the needle seat container 11 when the needle seat 2 is pressed onto the needle seat container 11 cooperating with the slidable button 3 as shown in FIG. 5 and FIG. 6.

Figure 8:
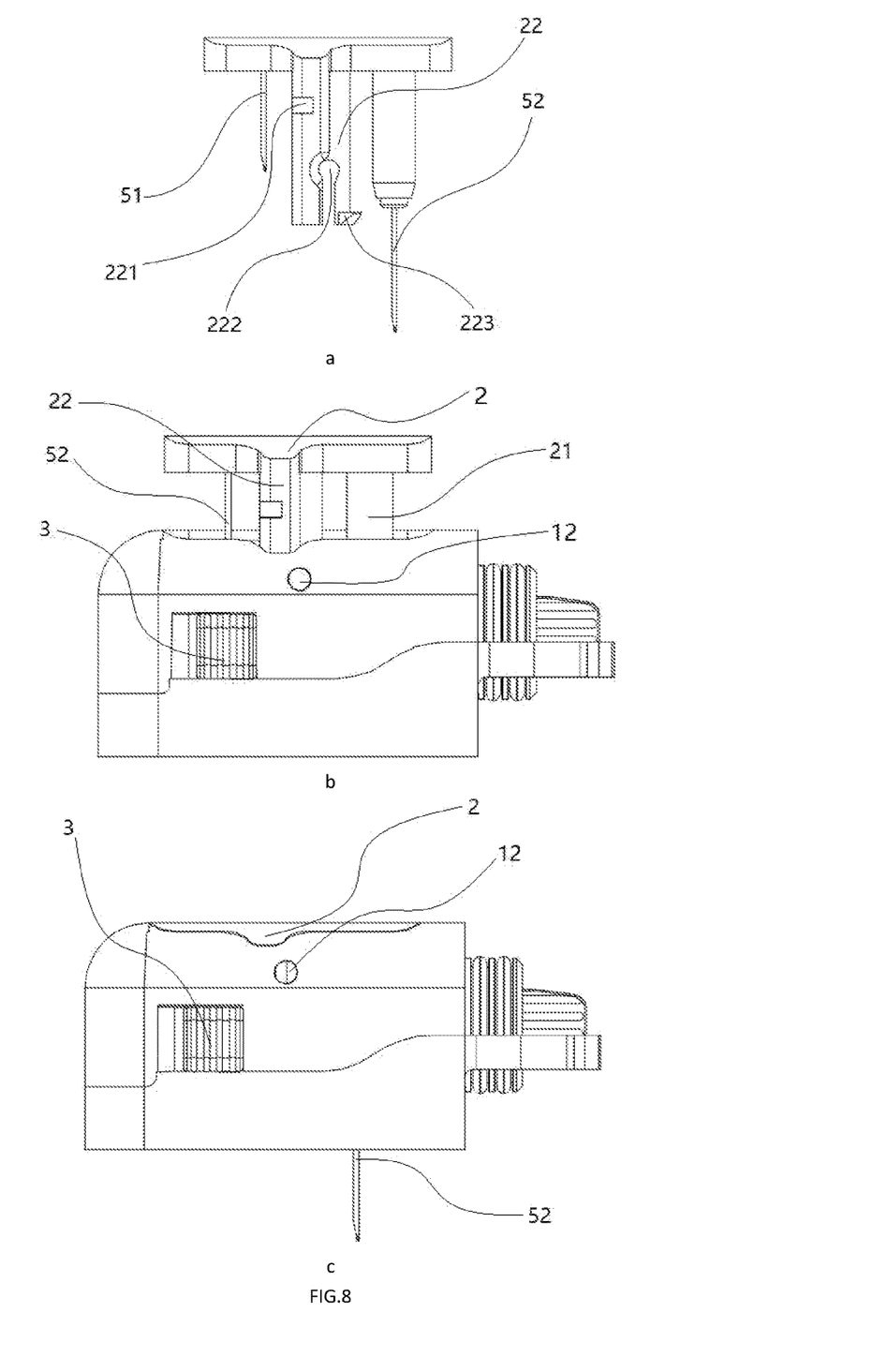
FIG. 8 is a perspective view of the needle seat and the housings of the delivery system of a portable delivery device in the present invention

FIG. 8 provides another side of view of how the needle seat 2 and the U-shape needle fixed on the needle seat 2 are coupled to the upper and lower housings. As shown in FIG. 8a, a slot 221 and a round slot 222 are further set on the multi-cavity column 22 of the needle seat 2; the slot 221 is configured to let the tiny hook 31 of the slidable button 3 as shown in FIG. 5 slip out of the cavity 24 in order to release the needle seat 2 from the needle seat container; and the round slot 222 is configured to mate with one kind of needle seat cover which will be mentioned later. Additionally, as shown in FIG. 8a, the multi-cavity column 22 has an outer rim 223 near the cavity 23 configured to lock the multi-cavity column 22 on the upper housing, preventing the needle seat 2 from being separated completely from the upper housing when at its initial position as shown in FIG. 8b. When the needle seat 2 is pressed onto the needle seat container and the long end 52 of the U-shape needle goes out of the lower housing as shown in FIG. 8c, the hook 31 of the slidable button 3 mates the cavity 24 of the multi-cavity column 22 to fix the needle seat 2 at its engaged position so the long end 52 of the U-shape needle stays out of the lower housing. At this time, the spring 42 around the column 41 on the lower housing is in its compressed status as shown in FIG. 7b.

Referring to FIG. 5, FIG. 7 and FIG. 8, when a withdrawal of the U-shape needle is needed, slide the slidable button 3 to match the tiny hook 31 with the slot 221 on the multi-cavity column 22, so the tiny hook 31 slips out of the cavity 24 and the multi-cavity 22 is no longer stuck by the tiny hook 31 resulting in the needle seat 2 being pulled out of the needle seat container on the upper housing back to its initial status by the column 41 via releasing the tension of the compressed spring 42 around the column 41, so the long end 52 of the U-shape needle is withdrawn into the lower housing.

Figure 9:
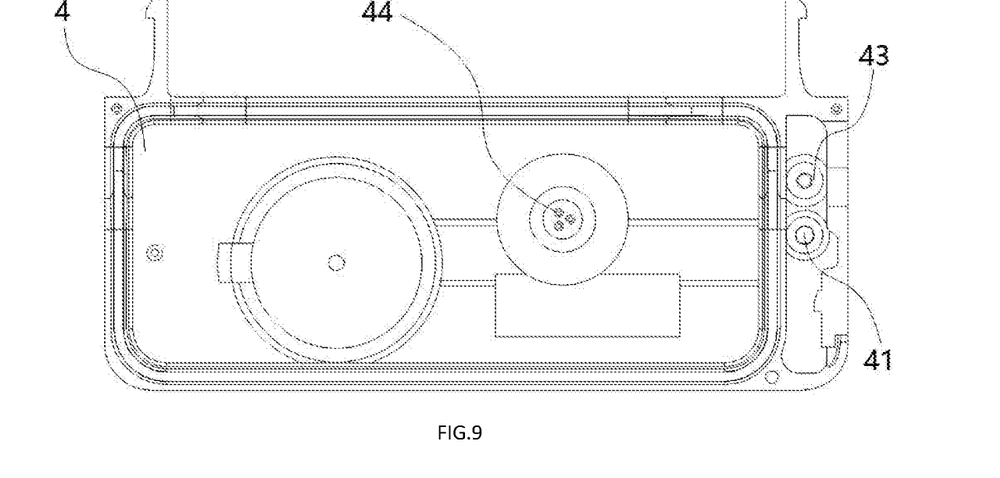
FIG. 9 is a perspective view 1 of the lower housing of the delivery system of a portable delivery device in the present invention

Referring to FIG. 9, three tiny holes 44 for air permeation are further set on the lower housing 4, configured to keep the pressure balance inside the housing during the delivery process.

Figure 10:
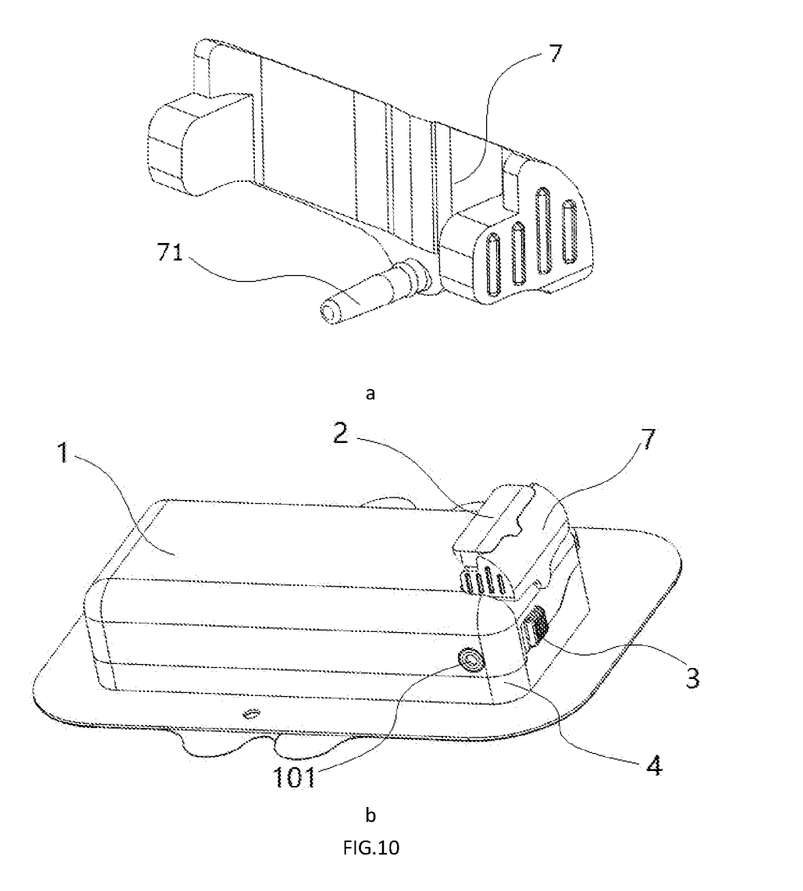
FIG. 10 is a perspective view 1 of the needle seat cover of the delivery system of a portable delivery device in the present invention

Referring to FIG. 10 and FIG. 8, an embodiment of a needle seat cover of the present invention is provided. As shown in FIG. 10a, a latch 71 is arranged on the needle seat cover 7. A hole 12 is set on the upper housing 1 as shown in FIG. 8b and FIG. 8c, and a round slot 222 is set on the multi-cavity column 22 as shown in FIG. 8a, and the two holes are overlapped at the initial position of the needle seat 2. When the latch 71 is inserted into the two holes, the needle seat cover 7 is stuck between the needle seat 2 and the needle seat container 11 of upper housing 1 as shown in FIG. 10b, so the needle seat 2 is fixed at its initial position which cannot be pressed onto the needle seat container accidentally.

Figure 11:
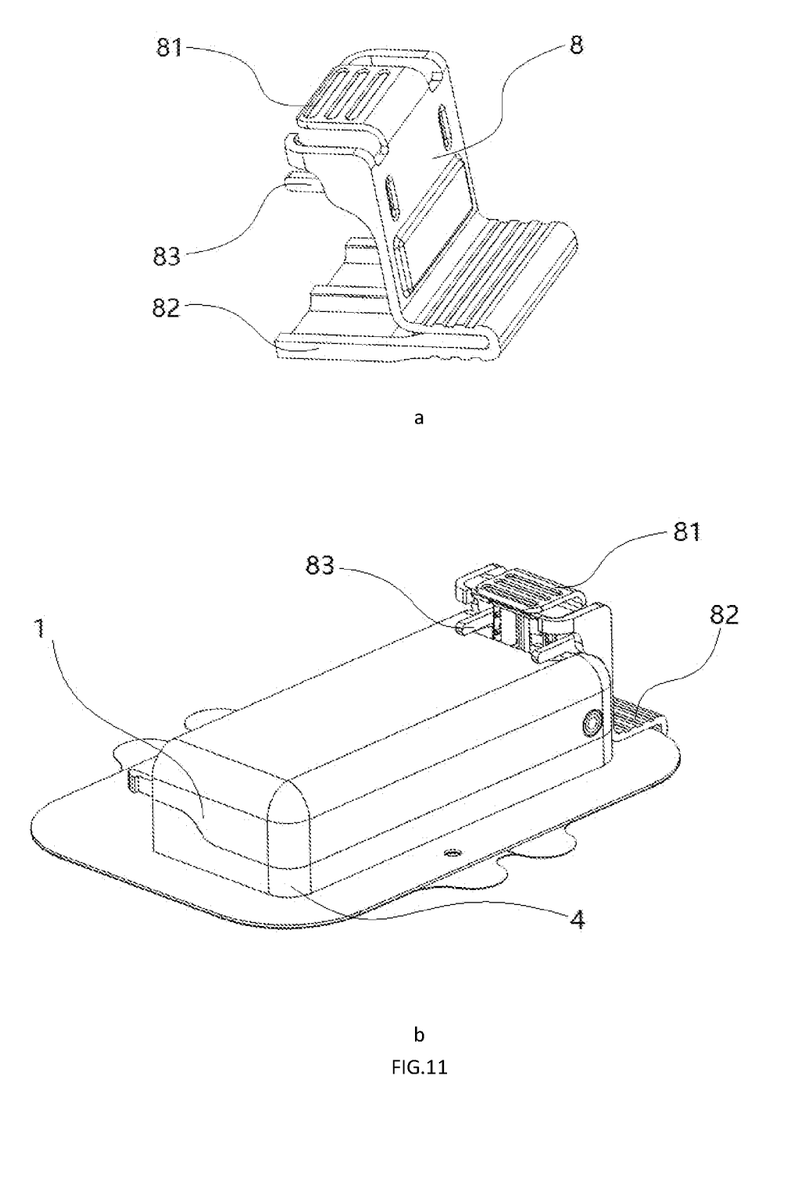
FIG. 11 is a perspective view 2 of the needle seat cover of the delivery system of a portable delivery device in the present invention

Referring to FIG. 11, FIG. 7 and FIG. 8, an embodiment of a different kind of needle seat cover of the present invention is provided. As shown in FIG. 11a, the needle seat cover 8 comprises a top part 81 to cover the upper surface of the needle seat 2, a bottom part 82 to cover the exit hole of the long end 52 of the U-shape needle on the lower housing as shown in FIG. 7, and two sticks 83 to lock on the upper housing 1. Before a drug fluid is delivered to a human body, the air in the lumen of the infusion needle should better be exhausted and the process of filling the drug fluid all over the lumen of the infusion needle is called priming. Pressing the top part 81 of the needle seat cover 8 after filling the reservoir makes the needle seat 2 go down a little instead of going down onto the needle seat container completely because the exit of the long end 52 of the U-shape needle on the lower housing 4 is blocked by the bottom cover 82. With the slight downward movement of the needle seat 2, the short end 51 of the U-shape needle shown in FIG. 8 penetrates the silicone key 103, connecting the lumen of the U-shape needle to the chamber with triple connections 10, resulting in the drug fluid filling the lumen of the U-shape needle from the chamber with triple connections 10. However, due to the bottom cover 82 blocking the exit of the long end 52 of the U-shape needle, the long end 52 would not go out of the lower housing and penetrate a human skin, so the priming is realized before delivering the drug fluid to a patient.

The above descriptions of the detailed embodiments are only to illustrate the principle and the effect of the present invention, and it is not to limit the scope of the present invention. Those skilled in the art can modify or change the embodiments without departing from the spirit and scope of the present invention. Accordingly, all equivalent modifications and variations completed by persons of ordinary skill in the art, without departing from the spirit and technical idea of the present invention, should fall within the scope of the present disclosure defined by the appended claims.

The invention claimed is:

1. A delivery system of a portable delivery device, comprising:
   an upper housing, comprising a chamber with triple connections to a syringe, a reservoir and an infusion needle; and
   a lower housing mating the upper housing, wherein
   the reservoir is arranged inside the upper housing and provided with a hole aligned with the chamber, and the reservoir is connected with the chamber through the hole.

2. The delivery system of a portable delivery device according to claim 1, wherein,
   the chamber with triple connections is connected with the syringe, the reservoir and the infusion needle by three elastic material components.

3. The delivery system of a portable delivery device according to claim 2, wherein,
   a hole is set on the elastic material element connecting the chamber with triple connections and the reservoir, mating the hole on the reservoir.

4. The delivery system of a portable delivery device according to claim 2, wherein,
   the elastic material components are silicone keys.

5. The delivery system of a portable delivery device according to claim 1, wherein,
   the infusion needle is a U-shape hollow needle.

6. The delivery system of a portable delivery device according to claim 5, wherein, the U-shape hollow needle is arranged on a needle seat which is installed on a needle seat container on the upper housing movably.

7. The delivery system of a portable delivery device according to claim 6, wherein,
   the U-shape hollow needle has two ends of different lengths;
   the short end is connected with the chamber with triple connections by penetrating the elastic material element, configured to allow the drug fluid to enter the lumen of the U-shape hollow needle from the chamber with triple connections;
   the long end of the U-shape hollow needle is able to penetrate a human skin through the upper housing and the lower housing, configured to deliver the drug fluid to human body from the lumen of the U-shape hollow needle.

8. The delivery system of a portable delivery device according to claim 6, wherein,
   the needle seat comprises a needle fixing column, configured to fix the long end of the U-shape hollow needle on the needle seat; further comprises a multi-cavity column with an outer rim;
   the needle seat container on the upper housing comprises two receiving cavities, one cylindrical cavity is configured to receive the needle fixing column; the other cavity is configured to receive the multi-cavity column and mate with the outer rim of the multi-cavity column, preventing the needle seat from being separated completely from the upper housing.

9. The delivery system of a portable delivery device according to claim 8, wherein,
   a slidable button with a tiny hook which releasably mate the multi-cavity column is further set on the upper housing, configured to control the position of the needle seat.

10. The delivery system of a portable delivery device according to claim 9, wherein,
    a spring is set around the column on the lower housing, cooperating with the slidable button, configured to retract the needle seat after the needle seat being pressed in order to withdraw the infusion needle into the lower housing.

11. The delivery system of a portable delivery device according to claim 8, wherein,
    the multi-cavity column has an irregular shape and comprises two cavities I and II;
    cavity I is configured to receive the column with the spring on the lower housing, and the multi-cavity column has an outer rim near cavity I configured to get the multi-cavity column stuck on the upper housing, preventing the needle seat from being separated completely from the upper housing;
    cavity II is configured to mate the tiny hook on the slidable button, and a slot is further arranged on the multi-cavity column from which the tiny hook can be released from cavity II.

12. The delivery system of a portable delivery device according to claim 8, wherein,
    a needle seat cover with a latch is releasably installed on the needle seat;
    a hole is set on the upper housing and a hole is set on the multi-cavity column of the needle seat;
    the two holes initially overlap each other and the latch is inserted in the two holes, configured to prevent the needle seat from being pressed improperly making the infusion needle protruding from the lower housing.

13. The delivery system of a portable delivery device according to claim 8, wherein,
    a needle seat cover is releasably installed half-covering the combined upper and lower housings;
    the top part of the needle seat cover covers the upper surface of needle seat, and the bottom part of the needle seat cover covers the exit hole of the infusion needle on the lower housing, preventing the infusion needle from protruding from the lower housing.

14. The delivery system of a portable delivery device according to claim 1, wherein,
    the lower housing comprises a column and a receiver with an exit hole which allows the infusion needle to go through.

15. The delivery system of a portable delivery device according to claim 1, wherein, the lower housing further comprises several tiny holes for air permeation use.

\* \* \* \* \*